May 1, 1962 G. MERRILL Plant Pat. 2,144

PEACH TREE

Filed April 27, 1961

WITNESS

Addison E. Avery

GRANT MERRILL
INVENTOR

HUEBNER & WORREL
ATTORNEYS

BY Richard M. Worrel

United States Patent Office

Plant Pat. 2,144
Patented May 1, 1962

2,144
PEACH TREE

Grant Merrill, P.O. Box 392, Red Bluff, Calif.

Filed Apr. 27, 1961, Ser. No. 106,138
1 Claim. (Cl. 47—62)

The present invention relates to a peach tree and more particularly to a new and distinct variety thereof broadly characterized by a large productive tree, with fruit which ripens very late in the season, having attractive mottled skin color, and highly flavored yellow flesh, which frees from the stone, is fine flavored, and does not darken on exposure to the air.

An object of my plant breeding procedures which led to the variety herein shown and described was to provide an improved peach tree of the late bearing type.

Another object was to provide a peach tree somewhat similar to the Merrill Pageant (Plant Patent No. 1,338) but bearing at a somewhat later date.

Another object was to provide a peach tree somewhat similar to said Merrill Pageant but larger, more productive and having fruit of better flavor and more attractive coloring.

Further objects and advantages will become more fully apparent in the subsequent description in the specification.

In the drawing which is a water color painting:

Figure 1:
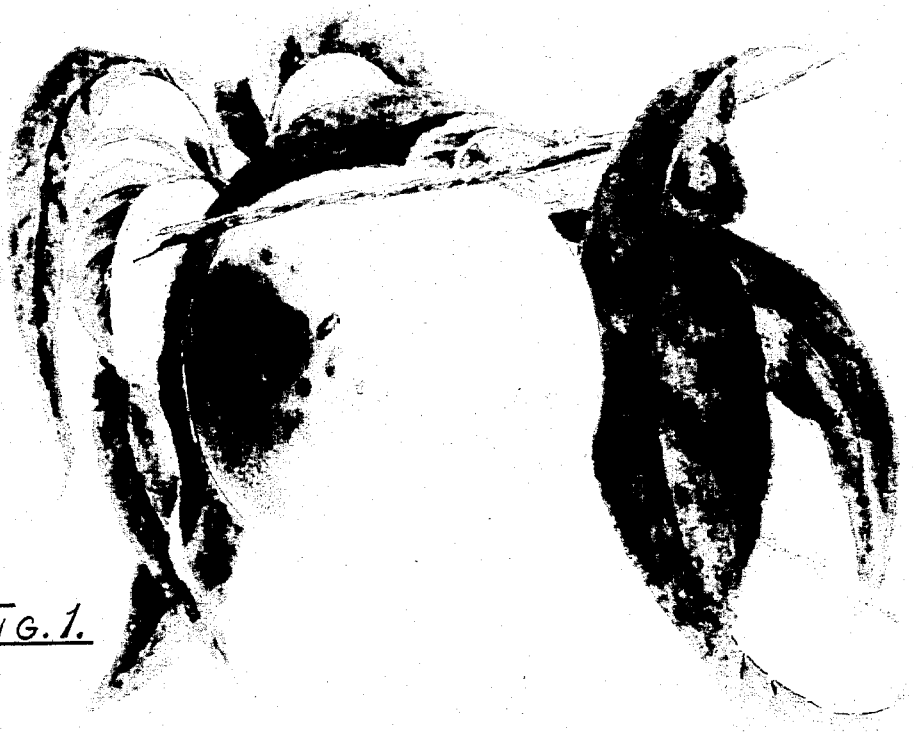
FIG. 1 shows a characteristic fruit bearing twig of the subject variety showing leaves and a mature peach thereon.
Figure 2:
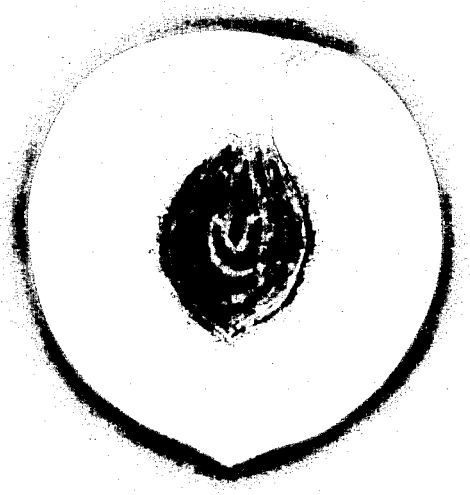
FIG. 2 shows a characteristic fruit of the variety divided on its suture plane to reveal flesh coloration with the pit in place therein.

The instant variety most nearly resembles the Merrill Pageant (Plant Patent No. 1,338) peach tree but is an improvement thereon in that its fruit has a more attractive mottled red skin, better flavored flesh and ripens from five to ten days later, depending on the weather, and has a larger more productive tree which blooms earlier.

This new variety of peach tree was produced by me on my plant breeding farm near Red Bluff, Tehama County, California, by crossing Merrill Rodeo (Plant Patent No. 1,097) with an open pollinated seedling from a tree which grew from a seedling resulting from a cross of July Elberta (Plant Patent No. 15) with Maxine (unpatented). Expressed by formula it would be: Merrill Rodeo × ((July Elberta × Maxine) × open pollinated).

The present variety was asexually propagated by grafting onto a tree of Merrill June (Plant Patent No. 869) growing on a farm at Lamont, Kern County, California. When the scion grafted into this tree came into bearing, the fruit and other characteristics proved to be identical with the original peach tree of the instant variety.

Referring more specifically to the pomological characteristics of this new and distinct variety of peach tree, the following have been observed under the ecological conditions prevailing at my farm near Red Bluff, Tehama County, California, and on a farm near Lamont, Kern County, California. All major color plate identifications are by reference to Maerz and Paul Dictionary of Color.

*Tree*

Shape: Medium size, medium vigor, moderately spreading, productive, regular bearer.

Trunk: Medium stocky, medium shaggy, grey in color. Lenticels—numerous and large.

Leaves (selected from mid-portions of vigorous unbranched terminal shoots 18" to 24" long):

*Length.*—5" to 7".

*Width.*—1" to 1 11/16".

*Form.*—Lanceolate, tip acuminate, medium thick.

*Color.*—Upper surface very dark green (23–L–3), under surface light green (21–K–6), midrib, greenish yellow (18–I–1).

*Class* (Meador and Blake: Proceedings Am. Soc. Hort. Sc., vol. 37, page 206).—Class 2 to 3. Length-width ratio—.21. Apex angle (1" from tip)—29° to 32°. Base angle (½" from petiole)—53° to 72°.

*Margin.*—Crenate.

*Petiole.*—Medium short, medium slender.

*Stipules.*—On young leaves, falling off early.

*Glands.*—Usually 2, sometimes 1 or 3, alternate, sometimes opposite, medium, reniform, yellow green, brown on older leaves, on petiole and sometimes on base of leaf.

Flowerbuds: Medium size, medium in length, obtuse, free, pubescent.

Flowers: Medium early bloom, about with July Elberta (Plant Patent No. 15), small, pink.

*Pollen.*—Abundant.

*Anthers.*—Red-orange.

*Fruit*

Maturity when described: Eating to firm ripe—approximately October 8 to October 13.

Size: Variable, medium to large.

*Axial diameter.*—2½" to 3½".

*Transverse in suture plane.*—2⅜" to 3½".

*At right angles to suture plane.*—2½" to 3⅜".

Form: Generally round.

*Suture.*—Distinct, shallow, extends from base to apex.

*Ventral surface.*—Light lipped toward apex on either side, lips usually slightly unequal.

*Cavity.*—Abrupt, elongated in suture plane, with suture usually showing on both sides. Depth ½" to ¾"; breadth ⅞" to 1¼". Markings usually yellow with red flecking.

*Base.*—Retuse.

*Apex.*—Rounded to mucronate, pistil point apical.

*Stem.*—Medium to short, length 3/16" to ¼", diameter ⅛" to 3/16". Does not usually adhere to stone.

Skin: Medium thick, medium tender, tenacious to flesh.

*Tendency to crack.*—None.

*Color.*—Undercolor, golden yellow (10–L–5) to orange yellow (10–I–7) with light red blush (3–K–10) overlaid with mottles of dark reddish-brown (7–L–7).

Flesh:

*Color.*—Golden yellow (9–L–3) near the stem end to orange yellow (9–L–6). Red (4–L–6) near stone, blending as it spreads outward into flesh to pink (2–I–3).

*Surface of pit cavity.*—Pink with white fibers.

*Amygdalin.*—Scant.

*Juice.*—Moderate.

*Texture.*—Firm, meaty to melting.

*Ripens.*—Evenly.

*Flavor.*—Mild, Delicate.

*Aroma.*—Distinct and delicate.

*Eating quality.*—Good to excellent.

Stone: Free with short fibers sometimes adhering to ridges. No adherence to flesh.

*Size.*—Medium; length 1½" to 1¾"; breadth ⅞" to 1⅛".

*Thickness.*—⅝" to ¾".

*Form.*—Lanceolate, tip acuminate.

*Base.*—Usually slightly oblique.

*Hilum.*—Oval.

*Sides.*—Usually unequal.

*Surface.*—Irregularly furrowed throughout. Ridged near base, pitted from base to above center. Ventral edge—thick without wings. Dorsal edge—full with furrows discontinuous toward tip.

*Color.*—When first exposed, red-brown (7–J–5) to darkest red-brown (8–L–5).

*Tendency to split.*—Slight.

Market: Local, dessert, long distance shipping, freezing.
Keeping quality: Good.

Although the new variety of peach tree possess the described characteristics under the growing conditions prevailing throughout most of the commercial peach producing areas of California, having been first observed near Red Bluff, California at the northern end of the Sacramento Valley and later confirmed by observation of the same variety near the Southern end of the San Joaquin Valley of California approximately four hundred miles farther south, it is to be understood that variations of the usual magnitude in characteristics incident to growing conditions, fertilization, pruning, thinning and pest control are to be expected.

Having thus described my new peach tree, what is claimed as new and desired to be secured by Letters Patent is:

A new and distinct variety of peach tree, substantially as illustrated and described, characterized by its large size and heavy production of fruit which ripens late in the season, is large, has beautifully mottled red skin, has flesh that frees from the stone, is highly flavored, attractive, and does not darken when exposed to air, and which most nearly resembles the Merrill Pageant (Plant Patent No. 1,338) peach tree, but is an improvement thereon by being a larger, more productive tree, blooming earlier, and producing fruit which ripens five to ten days later and is more attractively colored and better flavored.

No references cited.